United States Patent [19]

Regtop et al.

[11] Patent Number: 5,466,824
[45] Date of Patent: Nov. 14, 1995

[54] DIVALENT METAL COMPLEXES OF INDOMETHACIN, COMPOSITIONS AND MEDICAL METHODS OF USE THEREOF

[75] Inventors: Hubertus L. Regtop; John R. Biffin, both of New South Wales, Australia

[73] Assignee: Biochemical Veterinary Research Pty. Ltd., Australia

[21] Appl. No.: 217,520

[22] Filed: Mar. 24, 1994

Related U.S. Application Data

[63] Continuation-in-part of Ser. No. 773,601, Jan. 15, 1992, Pat. No. 5,310,936.

[30] Foreign Application Priority Data

May 22, 1989 [AU] Australia ................................. PJ4328

[51] Int. Cl.$^6$ ...................... C07D 209/28; A61K 31/555
[52] U.S. Cl. .......................... 548/402; 548/500; 548/501
[58] Field of Search ................................. 548/402, 500, 548/501

[56] References Cited

U.S. PATENT DOCUMENTS

| | | | |
|---|---|---|---|
| 3,669,987 | 6/1972 | Sato et al. | 260/326.14 X |
| 5,310,936 | 5/1994 | Regtop et al. | 548/501 |

FOREIGN PATENT DOCUMENTS

| | | |
|---|---|---|
| 6223 | 1/1980 | European Pat. Off. . |
| 245126 | 11/1987 | European Pat. Off. . |
| 405602 | 1/1991 | European Pat. Off. . |
| 73045 | 12/1977 | Romania . |
| 73044 | 12/1977 | Romania . |
| 448955 | 11/1977 | Spain . |
| WO90/14337 | 11/1990 | WIPO . |

OTHER PUBLICATIONS

Quellette et al Introduction to General, Organic, and Biological Chemistry 2nd Ed. (1990) p. 170.
Allinger et al., *Organic Chemistry*, p. 186 (1971).
Cunningham, in *McGraw–Hill Encyclopedia of Science & Technology*, 6th ed., pp. 483–484 (1987).
Russahov et al. *Acta Physiological et Pharm. Bulgaria* 36–42 (1986).
Singla et al., *Chemical Abstracts*, vol. 113, No. 7, abstract No. 65154 (Aug. 13, 1990).
Singla et al., *Int. J. Pharm.*, 1990, 60(1) 27–33.
Ivancheva et al., *Acta Physiol. Pharmacol. Bulgaria*, 14, 52 (1988).
Weser et al., *Biochim. Biophys. Acta*, 631, 232–45 (1980).
Flower et al., *The Pharmacological Basis of Therapeutics*, pp. 674–704 (Gilman et al. eds. 1985).
Shay et al., *Gastroenterology*, 5, 43–61 (1945).
Sorenson, *J. Med. Chem.*, 19, 135–48 (1976).

(List continued on next page.)

*Primary Examiner*—David B. Springer
*Attorney, Agent, or Firm*—Willian Brinks Hofer Gilson & Lione

[57] ABSTRACT

The present invention provides a process for the preparation of a complex of indomethacin and a divalent metal comprising forming a solution by dissolving indomethacin and a salt of said divalent metal in a tertiary amide or cyclic tertiary amide, adding a $C_{1-4}$ alkanol or $C_{3-6}$ ketone to the solution to precipitate the complex, and separating the precipitated complex from the solution. The present invention also provides a method for the treatment of inflammation or pain in a mammal requiring such treatment, comprising administering to said mammal an anti-inflammatory or analgesically effective amount of a complex of indomethacin and a divalent metal, the complex having the formula $[M]_2[\text{indomethacin}]_4[S]_n$, wherein M is the divalent metal, S is a molecule of a tertiary amide or a cyclic tertiary amide, and n is 2 or 3, or of a pharmaceutical composition comprising said complex together with a pharmaceutically acceptable carrier, diluent and/or excipient. The present invention further provides a complex of indomethacin and a divalent metal, the complex having the formula $[M]_2[\text{indomethacin}]_4[S]_n$, wherein M, S, and n are defined above, and a pharmaceutical composition comprising this complex together with a pharmaceutically acceptable carrier, diluent and/or excipient.

14 Claims, No Drawings

OTHER PUBLICATIONS

Sorenson et al., *Biol. Trace Element Res.*, 5, 257–73 (1983).
Barbu et al., *Chemical Abstracts*, vol. 100, No. 13, abstract No. 103177 (Mar. 26, 1984).
Barbu et al., *Chemical Abstracts*, vol. 99, No. 13, abstract No. 105123 (Sep. 26, 1983).
Rusanov et al., *Chemical Abstracts*, vol. 109, No. 17, abstract No. 142549 (Oct. 24, 1988).
Rusanov et al., *Acta Physiol. Pharmacol. Bulg.*, 1988, 14(1), 52–9.
Ogiso et al., *Chemical And Pharmaceutical Bulletin*, vol. 36, No. 2, 1988, pp. 757–762.
Lewis et al., *Chemical Abstracts*, vol. 96, No. 17, abstract No. 135522 (Apr. 26, 1982).
Lewis et al., *Agents Actions Supp.*, 1981, 8 (Trace Elem. Pathog. Treat. Inflammation), 339–58.
Adsara Dalmau, *Chemical Abstracts*, vol. 89, No. 21, abstract No. 186070 (Nov. 20, 1978).

DIVALENT METAL COMPLEXES OF INDOMETHACIN, COMPOSITIONS AND MEDICAL METHODS OF USE THEREOF

This application is a continuation-in-part of application Ser. No. 07/773,601 filed Jan. 15, 1992 now U.S. Pat. No. 5,310,936.

The present invention relates to a process for the preparation of complexes of indomethacin and divalent metals, and more particularly to an efficient process for the preparation of copper-indomethacin complexes.

The invention also relates to a composition containing a complex of indomethacin and a divalent metal and more particularly to an oral composition containing copper-indomethacin complexes.

The invention further relates to a method for the treatment of various conditions in mammals and in particular to shin soreness and other musculo-skeletal inflammation in mammals, including man, and more particularly to the treatment of those conditions in horses.

BACKGROUND

Present medical treatment of shin soreness and other musculo-skeletal inflammation in horses involves mainly administration of nonsteroidal anti-inflammatory drugs (NSAIDs). For example, phenylbutazone has been the definitive drug used in the race horse industry for many years. However, phenylbutazone has a long and unpredictable excretion and, while the pharmacological actions of this drug may be complete within 24 hours, undesirable detection may continue in plasma and urine for long periods after cessation of treatment. This is of importance to animals required to compete drug-free. Furthermore, phenylbutazone has established and widely reported gut toxicity in the horse.

Indomethacin [1-(p-chlorobenzoyl)-5-methoxy-2-methylindole-3-acetate] has a half-life of 2 to 11 hours which means it must be administered 2 to 3 times daily to be effective [Flower, R. J., Moncado, S., and Vane, J. R., Analgesic-Antipyretics and Anti-Inflammatory Agents: Drugs employed in the treatment of gout. In "The Pharmacological Basis of Therapeutics" (7th Ed., Eds. Gilman, A. G., Goodman, L. S., Rall, T. W., and Murad, F., MacMillan, New York, 1985)].

While it is known that indomethacin has an anti-inflammatory action, it is also known that it causes gastrointestinal reactions in some mammals, e.g. dogs and humans. These reactions include single or multiple ulcerations of the esophagus, stomach and duodenum. Attempts to reduce these gastrointestinal effects have been made by taking the oral drug immediately after meals, with food, milk or antacids, or antiulcer compounds.

NSAIDs also have an analgesic effect which is partly a result of, and partly dissociated from, their anti-inflammatory action. This dissociation varies from drug to drug. Thus, analgesia obtained from phenylbutazone and, to a lesser extent indomethacin, is primarily a result of its anti-inflammatory action.

Certain complexes of indomethacin and divalent metals are known. See Sorenson, *J. Med. Chem.*, 19, 135–148 (1976); ES 448,955 (November 1977); *Chemical Abstracts*, 89, 375 (abs. no. 186070) (1978); Weser et al., *Biochim. Biophys. Acta*, 631, 232–245 (1980); Lewis et al., *Agents Actions Suppl.*, 8 (Trace Elem. Pathog. Treat. Inflammation), 339–58 (1981); Romanian 73 044 (Dec. 28, 1982); Romanian 73 045 (Oct. 30, 1982); Sorenson et al., *Biol. Trace Elem. Res.*, 5, 257–273 (1983); *Chemical Abstracts*, 99, 574 (abs. no. 105123) (1983); *Chemical Abstracts*, 100, 635 (abs. no. 103177) (1984); Ivancheva et al., *Acta Physiol. Pharmacol. Bulgarica*, 14, 52–59 (1988); Singla et al., *Int'l J. Phamaceutics*, 60, 27–33 (1990). Some of these complexes have been reported to have anti-inflammatory, anti-arthritic or analgesic activity. See ES 448,955; *Chemical Abstracts*, 89, 375 (abs. no. 186070) (1978); Lewis et al., *Agents Actions Suppl.*, 8 (Trace Elem. Pathog. Treat. Inflammation), 339–58 (1981); Romanian 73 044; Romanian 73 045; *Chemical Abstracts*, 99, 574 (abs. no. 105123) (1983); *Chemical Abstracts*, 100, 635 (abs. no. 103177) (1984).

In particular, Weser et al., *Biochim. Biophys. Acta*, 631, 232–245 (1980) teaches $copper_2indomethacin_4((CH_3)_2SO)_2$ complexes. The yield of these complexes obtained by Weser et al. is very poor (2%; see page 233). Also, the presence of the dimethyl sulfoxide in the complexes renders them unsuitable for pharmacological use. These complexes have, consequently, only been laboratory items of no apparent benefit to man or domestic animals. Weser et al. also teaches $copper_2indomethacin_4(H_2O)_2$ complexes, but no method of preparing these complexes is specified.

Okuyama et al., *Agents and Actions*, 21, 130–144 (1987) reports that $copper_2indomethacin_4$ complexes prepared as described in Sorenson, *J. Med. Chem.*, 19, 135–148 (1976) are more effective as analgesics than is indomethacin or morphine in the writhing mouse and adjuvant arthritic rat pain models. Sorenson, *J. Med. Chem.*, 19, 135–148 (1976) reports that these complexes have the formulas $copper_{2n}indomethacin_{4n}((CH_3COCH_3)_{2n}$ and $copper_{2n}indomethacin_{4n}(H_2O)_{4n}$ (see Table IV) and suggests a binuclear structure for them (see page 141). Sorenson, *J. Med. Chem.*, 19, 135–148 (1976) also reports that the $copper_{2n}indomethacin_{4n}((CH_3COCH_3)_{2n}$ and $copper_{2n}indomethacin_{4n}(H_2O)_{4n}$ complexes have anti-ulcer activity (see Table IV). See also Sorenson et al., *Biol. Trace Elem. Res.*, 5, 257–273 (1983) which reports that $copper_2indomethacin_4$ $((CH_3COCH_3)_2$ complexes have anti-ulcer activity. No method for the preparation of the $copper_2indomethacin_4((CH_3COCH_3)_2$ complexes is taught by Sorenson et al., *Biol. Trace Elem. Res.*, 5, 257–273 (1983).

DISCLOSURE OF THE INVENTION

According to one broad form of the invention, there is provided a process for the preparation of large quantities of indomethacin-divalent metal complexes. The process comprises the following steps:

forming a solution of indomethacin and of a salt of the divalent metal in a tertiary amide of the following formula:

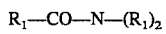

or in a cyclic tertiary amide (N-substituted lactam) of the following formula:

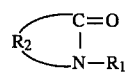

wherein $R_1$ is an alkyl having from 1 to 4 carbon atoms, and each $R_1$ may be the same or different, and $R_2$ is a cycloalkyl having from 2 to 7 carbon atoms;

adding a $C_{1-4}$ alkanol or $C_{3-6}$ ketone to the solution to precipitate the complex; and separating the precipitated complex from the solution.

The divalent metal salt used in the preparation of the indomethachin-divalent metal complexes is preferably the acetate, more preferably the acetate monohydrate, and most preferably cupric acetate monohydrate.

According to another broad form of this invention there is provided a method for the treatment of inflammation or pain in a mammal requiring such treatment. The method comprises administering to said mammal an anti-inflammatory or analgesically effective amount of a complex of indomethacin and a divalent metal, the complex having the formula

wherein

M is the divalent metal;

X is a molecule of a tertiary amide of the following formula:

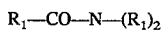

or of a cyclic tertiary amide (N-substituted lactam) of the following formula:

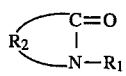

wherein $R_1$ is an alkyl having from 1 to 4 carbon atoms, and each $R_1$ may be the same or different, and $R_2$ is a cycloalkyl having from 2 to 7 carbon atoms; and n is 2 or 3.

The indomethacin-divalent metal complex or the pharmaceutical composition containing it, may be administered orally, parenterally, rectally, or topically as described below.

According to yet another broad form of this invention there is provided a pharmaceutical composition for alleviating inflammation and pain. The composition comprises:

a pharmaceutically acceptable carrier, diluent, excipient or combinations thereof; and a complex of indomethacin and a divalent metal, the complex having the formula

wherein

M is the divalent metal;

X is a molecule of a tertiary amide of the following formula:

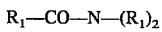

or of a cyclic tertiary amide (N-substituted lactam) of the following formula:

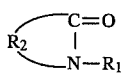

wherein $R_1$ is an alkyl having from 1 to 4 carbon atoms, and each $R_1$ may be the same or different, and $R_2$ is a cycloalkyl having from 2 to 7 carbon atoms; and n is 2 or 3.

Finally, the invention provides novel complexes of indomethacin and divalent metals having the formula:

wherein

M is the divalent metal;

X is a molecule of a tertiary amide of the following formula:

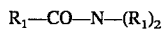

or of a cyclic tertiary amide (N-substituted lactam) of the following formula:

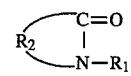

wherein $R_1$ is an alkyl having from 1 to 4 carbon atoms, and each $R_1$ may be the same or different, and $R_2$ is a cycloalkyl having from 2 to 7 carbon atoms; and n is 2 or 3.

The divalent metal in all of the above formulas is preferably copper, zinc, cobalt or nickel, and is more preferably copper. The tertiary amide or cyclic tertiary amide may be dimethylformamide, N-methylpyrrolidone and/or dimethyl acetamide, but is preferably dimethylformamide.

Generally the process for the preparation of the indomethacin-divalent metal complexes comprises: adding a solution of indomethacin to a solution of a divalent metal salt, such as the acetate monohydrate, and warming; adding a $C_{1-4}$ alkanol or $C_{3-6}$ ketone with agitation to the solution; allowing the solution to stand; harvesting the resultant precipitate; washing the precipitate with the same alkanol or ketone used in the last addition step; and drying the precipitate.

The tertiary amide or cyclic tertiary amide is generally dimethylformamide, N-methylpyrrolidone and/or dimethyl acetamide.

Typically the solution of indomethacin is heated prior to addition to the divalent metal salt solution to between about 30° C. and about 90° C. and more preferably heated to about 50° C.

The mixture of indomethacin and the divalent metal salt is preferably warmed to between about 50° C. and about 90° C. and is preferably warmed to about 80° C.

The alkanol or ketone is preferably added with agitation to the solution of indomethacin and divalent metal salt.

The alkanol which is added to the mixture of indomethacin and the divalent metal salt and which is subsequently used to wash the precipitate is preferably ethanol or methanol and more preferably ethanol.

$C_3$-alkanol also includes propanol and isopropanol and $C_4$-alkanol includes butanol, sec butanol and tert butanol.

An example of a $C_{3-6}$ ketone is acetone.

The period for which the resultant solution is allowed to stand is from about eight hours to about four days and is preferably about one day.

The indomethacin-divalent metal complexes formed by the process of the invention have the formula:

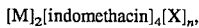

wherein

M is the divalent metal;

X is a molecule of a tertiary amide of the following formula:

or of a cyclic tertiary amide (N-substituted lactam) of the following formula:

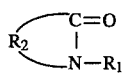

wherein $R_1$ is an alkyl having from 1 to 4 carbon atoms, and each $R_1$ may be the same or different, and $R_2$ is a cycloalkyl having from 2 to 7 carbon atoms; and n is 2 or 3.

The divalent metal in this formula is preferably copper, zinc, cobalt or nickel, and is more preferably copper. The tertiary amide or cyclic tertiary amide may be dimethylformamide, N-methylpyrrolidone and/or dimethyl acetamide, but is preferably dimethylformamide. Thus, the most preferred complex according to the invention is copper$_2$indomethacin$_4$dimethylformamide$_{2-3}$.

The indomethacin-divalent metal complexes as such, or formulated into pharmaceutical compositions, may be administered to mammals for alleviating inflammation and pain. To prepare the pharmaceutical compositions of the invention, the complexes are combined with a pharmaceutically acceptable carrier, diluent, excipient, or combinations thereof. The complexes or pharmaceutical compositions of the present invention may be administered orally, parenterally, rectally, or topically.

Liquid dosage forms for oral administration may include pharmaceutically acceptable emulsions, syrups, solutions, suspensions, and elixirs containing inert diluents commonly used in the art, such as water. Such compositions may also comprise wetting agents, emulsifying and suspending agents, and sweetening, flavoring, and perfuming agents including: sugars such as sucrose, sorbitol, fructose, etc.; glycols such as polyethylene glycol, propylene glycol, etc.; oils such as sesame oil, olive oil, soybean oil, etc.; antiseptics such as alkylparahydroxybenzoate, etc.; and flavors such as strawberry flavor, peppermint, etc.

The oral composition may be presented as a paste which is the preferable presentation when administered to horses.

If the preparation is presented as a paste, the indomethacin-divalent metal complex is preferably mixed in a thickening agent and preservative. A preferred thickening agent is carbopol and preferred preservatives are sodium propyl hydroxybenzoate or methyl paraben and propyl paraben.

Preferably the amount of indomethacin-divalent metal complex in the paste administered is in the range of from about 0.03 to about 0.5, and preferably from about 0.1 to about 0.2, mg per kg of a mammal. The method of treatment of the invention may also be applied to the following mammals: man, horses, dogs, and any other domestic animal.

Solid dosage forms for oral administration may include capsules, tablets, pills, powders, and granules. In such solid dosage forms, the indomethacin-divalent metal complexes may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

When the preparation is presented as a tablet, any well known compound which increases the flow properties of the preparation is suitable and may be disodium phosphate or magnesium stearate, and preferably is disodium phosphate.

"Parenteral" as used herein includes subcutaneous injections, intravenous, or intramuscular injection, or infusion techniques.

When presented as an injectable preparation, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions can be prepared as suppositories for rectal administration by mixing the composition with a suitable non-irritating excipient such as cocoa butter and polyethylene glycols which are solid at ordinary temperatures but liquid at the rectal temperature and will therefore melt in the rectum and release the drug.

The compositions can be prepared as sprays or pastes for topical administration. The pastes may be prepared as described above. Sprays may be prepared by mixing the complexes with suitable non-toxic, pharmaceutically acceptable carriers, diluents, and/or excipients as known in the art.

Sore feet; bursitis; inflammation of joints; minor sprains and muscle soreness; splint exostosis; navicular disease; ringbone (non-articular); osselets (non-articular); back problems and prevention of serious injuries in horses in training and racing, may be treated with preparations of this invention.

It has been found that the copper$_2$indomethacin$_4$ complexes of the invention have a half-life of 23 to 25 hours thus making a single daily dose effective. By contrast, indomethacin and the prior art copper$_1$indomethacin$_2$ complexes must be administered every eight hours. Additionally, the copper$_2$indomethacin$_4$ complexes of the invention have a potent analgesic effect independent of the analgesic effect resulting from its anti-inflammatory action, unlike phenylbutazone and indomethacin itself.

It has surprisingly been found by the inventors that copper$_2$indomethacin$_4$ complexes of the invention are effectively metabolized, and undesirable urine levels are undetectable 72 hours after the last dose, for example, in horses. Preliminary trials indicate that this also holds true for humans and greyhounds.

It has also been found by the inventors that the copper$_2$indomethacin$_4$ complexes of the invention are relatively non-toxic to the gut of dogs at far higher than therapeutic levels, while the same dose of indomethacin is severely toxic.

It has further been found by the inventors that a 5X effective dose of the copper$_2$indomethacin$_4$ complexes of the invention are non-toxic to the gut and central nervous system (CNS) of horses, while a 1X and 5X effective dose of phenylbutazone is toxic to the gut, and a 5X effective dose of indomethacin is toxic to the CNS.

In general, it has been found that the copper$_2$indomethacin$_4$ complexes of the invention are between 10- and 30-fold less toxic than indomethacin or copper$_1$indomethacin$_2$ complexes.

It has also been found by the inventors that the copper$_2$indomethacin$_4$ complexes of the invention have significant non-ulcerogenic activity when tested for anti-ulcer activity in the Shay ulcer model (Shay et al., *Gastroenterology*, 5, 43–61 (1945)).

Finally, the inventors have found that the $copper_2indomethacin_4$ complexes of the invention are between 10- and 20-fold more potent than $copper_1indomethacin_2$ complexes or indomethacin itself.

The following table sets out a comparison of certain properties of indomethacin, the $copper_1indomethacin_2$ complexes of ES 448,955 and RO 73,045, the $copper_{2n}indomethacin_{4n}(H_2O)_{4n}$ complexes of Sorenson, *J. Med. Chem.*, 19, 135–148 (1976), and the $copper_2indomethacin_4dimethylformamide_{2-3}$ complex of the present invention.

| Compound | Property | | |
|---|---|---|---|
| | Molecular Weight | Melting Point (°C.) | Effective Dose (mg/kg) |
| Indomethacin | 357.81 | 162 | 1–4 |
| Copper$_1$ indomethacin$_2$ (ES 448955) | 777.13 | 200 | 1–5 |
| Copper$_1$ indomethacin$_2$ (H$_2$O)$_2$ (RO 73045) | 813 | 196 | n/a |
| Copper$_{2n}$ indomethacin$_{4n}$ (H$_2$O)$_{4n}$ (Sorenson (1976)) | | 190–193 | |
| Copper$_2$ indomethacin$_4$ dimethylformamide$_{2-3}$ (invention) | 1677 | 246 | 0.1–0.2 |

BEST MODE AND OTHER MODES FOR CARRYING OUT THE INVENTION

An effective amount of $copper_2indomethacin_4dimethylformamide_{2-3}$ to achieve a desired level of analgesia and decrease in inflammation is administered orally to a horse. The composition for this purpose is presented to the horse as a paste which is prepared as follows. Carbopol is dissolved in distilled water. Sodium propyl hydroxybenzoate or methyl paraben and propyl paraben are then added to the carbopol mixture. The mixture is then heated to achieve dissolution of the three compounds. The pH is then adjusted with alkali to a value of between about 5.5 and about 6.5 which causes the thickness and viscosity of the carbopol to increase to the extent that a paste is formed.

The $copper_2indomethacin_4$-dimethylformamide$_{2-3}$ is mixed with the paste mechanically to form a homogeneous smooth green-blue composition.

The specific dose level for a particular horse will depend on a variety of factors including age, general health, sex, diet, body weight and time of administration.

The present invention will now be described with reference to the following examples which should not be construed as limiting on the scope thereof.

EXAMPLE 1

PREPARATION OF COPPER$_2$INDOMETHACIN$_4$

To a warm (about 50° C.) solution of 142 g of indomethacin in dimethylformamide (200 ml) was added a solution of cupric acetate monohydrate (40 g) in dimethylformamide (250 ml) and heated to 80° C. Ethanol (2.5 liters) was added to the mixture with vigorous shaking and the deep green solution kept for about 1 day during which time the copper-indomethacin complex separated as a microcrystalline green powder. The mixture was filtered under vacuum and the green product was washed exhaustively with ethanol (1 liter), dried at room temperature overnight and further dried at 100° C. for 3 hours. Yield was 145 g (79.6%) which represented complexing of 7.1 g indomethacin per 100 ml solute.

The composition and crystal structure of this complex produced by this method were determined by X-ray diffraction. For diffractometry a crystal of dimensions 0.10×0.15×0.15 mm was mounted on a glass fiber with cyanoacrylate resin. Lattice parameters at 21° C. were determined by a least-squares fit to the setting parameters of 25 independent reflections, measured and refined on an Enraf-Nonius CAD4F four-circle diffractometer employing graphite monochromated MoK$\alpha$ radiation.

Crystal data—Formula $C_{80}H_{71}Cl_4Cu_2N_4O_{20}$; M 1677.2, triclinic, space group P1, a 10.848(3), b 13.336(6), C 16.457(4) Å, $\alpha$ 104.67(3), $\beta$ 100.94(2), $\gamma$ 107.16(3)°, V2109(2) Å$^3$, Z 1, D$_c$ 1.321 g cm$^{-3}$, $\mu$(MoK$\alpha$) 6.88 cm$^{-1}$, $\lambda$(MoK$\alpha$) 0.7107 Å, F (000) 865 electrons.

Intensity data were collected in the range $1<\Theta<21°$ using an $\omega$-0.67$\Theta$ scan. The scan widths and horizontal counter apertures employed were (1.30+0.35tan$\Theta$)° and (2.30+0.5tan$\Theta$) mm. Data reduction and application of Lorentz, polarization and decomposition (6.4%) corrections were carried out using the Enraf-Nonius Structure Determination Package, Enraf Nonius, Delft, 1985. Of the 4572 independent non-zero reflections collected, 2744 with I>2.5$\sigma$(I) were considered observed and used in the calculations.

The structure was solved by direct methods using SHELXS-86 (Enraf-Nonius Structure Determination Package), and the solution was extended by difference Fourier methods. Hydrogen atoms were included at sites calculated assuming tetrahedral geometry at carbon and nitrogen (C—H 0.97 Å) with group isotropic thermal parameters and all other atoms with the exception of minor contributors to disordered species (dimethyl formamide molecules) were refined anisotropically.

Blocked-matrix least-squares refinement of an overall scale factor, positional and thermal parameters converged (all shifts<0.40$\sigma$) with R* 0.046, R$_w$ 0.048 and w=0.75/($\sigma^2$(F$_o$)+0.0010F$_o^2$) [* R=$\Sigma$(||F$_o$|–|F$_c$||) /$\Sigma$|F$_o$|, R"=$\Sigma$(w$^{1/2}$||F$_o$|–|F$_c$||)/$\Sigma$w $^{1/2}$|F$_o$|]. Maximum excursions in a final difference map were +0.33eÅ$^{-3}$ and –0.25eÅ$^{-3}$. Scattering factors and anomalous dispersion terms used for Cu (neutral Cu) were taken from International Tables (International Table For X-Ray Crystallography, Volume 4, (Kynoch Press, Birmingham, 1974)) and all others used were those supplied in SHELX-76. (Sheldrick, G. M., SHELX-76, A Program For X-Ray Crystal Structure Determination, University of Cambridge, 1976). All calculations were carried out using SHELX-76, and plots were drawn using ORTEP (Johnson, C. K. ORTEP, A Thermal Ellipsoid Plotting Program, Oak Ridge National Laboratories, Oak Ridge, 1965).

From the various measurements and calculations, it was determined that the structure of the copper-indomethacin complex produced by the above method consists of two copper atoms linked by four indomethacin groups. There is also a dimethylformamide molecule tightly bound to each of the copper atoms. A futher dimethylformamide molecule is loosely held in the lattice. This latter dimethylformamide site was found to be highly mobile and only partially occupied. During the data collection some decomposition of the intensities of the standard reflections was noted, and this is consistent with slow loss of this dimethylformamide molecule. Thus, the complex has the formula copper$_2$indomethacin$_4$dimethylformamide$_{2-3}$. The fused and conjugated five- and six-membered rings are close to being coplanar (deviations less than 0.04 Å). It is notable that the copper-dimer makes no close contacts with other molecules in the lattice. Therefore, the complex is hydrophobic.

The X-ray powder diffraction pattern of the copper$_2$indomethacin$_4$-dimethylformamide$_{2-3}$ complex was compared with the X-ray powder diffraction patterns of the copper$_{2n}$indomethacin$_{4n}$(H$_2$O)$_{4n}$ complexes prepared as described in Sorenson, *J. Med. Chem.*, 19, 135–148 (1976), and the copper$_2$indomethacin$_4$((CH$_3$)$_2$SO)$_2$ complexes prepared as described in Weser et al., *Biochim. Biophys. Acta.*, 631, 232–45 (1980). The X-ray diffraction patterns were recorded on a Siemens DS8000 diffractometer using Cu Kα radiation. Samples were briefly ground in a mortar and pestle and pressed into PTFE sample holders.

It was apparent from the X-ray diffraction patterns that the three samples were different. The observed differences were not those expected from the presence of residual solvent molecules simply cocrystallizing with the indomethacin and copper, but rather indicated that the solvent plays an essential part in determining the solid state structures of the three indomethacin-divalent metal complexes.

The six most intense peaks given as d values are listed in Table 1:

TABLE 1

| Copper$_2$ indomethacin$_4$ methyl- formamide$_{2-3}$ (invention) | Copper$_{2n}$ indomethacin$_{4n}$ (H$_2$O)$_{4n}$ (Sorenson (1976)) | Copper$_2$ indomethacin$_4$ ((CH$_3$)$_2$SO)$_2$ (Weser et al.) |
|---|---|---|
| 5.979 | 7.464 | 6.685 |
| 4.139 | 4.050 | 4.160 |
| 5.069 | 3.706 | 4.973 |
| 7.630 | 6.037 | 8.414 |
| 4.771 | 5.654 | 5.894 |
| 4.464 | 5.334 | 6.331 |

EXAMPLE 2

PRESENTATION OF COPPER$_2$INDOMETHACIN$_4$ AS A PASTE

Carbopol was dissolved in distilled water to a concentration of 1%. Methyl paraben and propyl paraben were added to a final concentration of 0.3% and 0.1% respectively; or sodium propyl hydroxybenzoate added to a final concentration of 0.45%. The mixture was heated to dissolve the above compounds. Sodium hydroxide was then added to adjust the pH to between about 5.5 to about 6.5. At this pH the thickness and viscosity of the carbopol increased dramatically to form a paste.

Copper$_2$indomethacin$_4$ prepared as described in Example 1 was then added, and the composition was mechanically mixed to form a smooth green-blue paste. It is necessary to add the copper-indomethacin complex after the paste has formed since addition prior to pH adjustment would prevent cross-linking of carbopol and make formation of a paste impossible.

EXAMPLE 3

PRESENTATION OF COPPER$_2$INDOMETHACIN$_4$ AS TABLETS

Copper$_2$indomethacin$_4$ prepared as described in Example 1 (200 mg) was added to disodium phosphate (300 mg) or dipac (300 mg) and magnesium stearate (5 mg). This was then mixed to a uniform powder and added to a rotary tablet maker.

EXAMPLE 4

PRESENTATION OF COPPER$_2$INDOMETHACIN$_4$ AS A TOPICAL PREPARATION

Copper$_2$indomethacin$_4$ prepared as described in Example 1 (1 g) and dimethyl sulphoxide (DMSO) (20 ml) were mixed and thickened by addition of glycerol (20 ml) and solid carbopol (60 g), prepared as in Example 2. This was blended into a paste which was able to be used as a topical preparation.

EXAMPLE 5

ABSORPTION OF COPPER$_2$INDOMETHACIN$_4$ PASTE

Four mares, A, B, C and D, bodyweight 420–455 Kg, were administered 200 mg of copper$_2$indomethacin$_4$ prepared as described in Example 1 by oral paste, and blood was taken for analysis by HPLC one hour later.

| HORSE | COPPER$_2$INDOMETHACIN$_4$ (ng/ml) |
|---|---|
| A | 140 |
| B | 210 |
| C | 81 |
| D | 88 |

EXAMPLE 6

TOXICITY AND EFFICACY OF COPPER$_2$INDOMETHACIN$_4$ PASTE

Four mares were administered 200 mg of copper$_2$indomethacin$_4$ prepared as described in Example 1 by oral paste daily for 7 days and observed for changes in clinical signs. No effects were noted in mares A, B, and D. Mare C had sustained a lacerated hoof, heel and coronet between Example 5 and Example 6, and was unable to bear weight on the limb. By day 3 she was sound, and by day 9 severely lame again.

EXAMPLE 7

BIOAVAILABILITY STUDIES ON HORSES

Horses were dosed with 200 mg of copper$_2$indomethacin$_4$ prepared as described in Example 1 in a paste of 1% carbopol in 0.3% methyl paraben and 0.1% propyl paraben, given orally. Indomethacin was detected in the urine and plasma of horses as follows.

| TIME (hours) | COPPER$_2$INDOMETHACIN$_4$ | |
| --- | --- | --- |
| | Urine (μg/ml) | PLASMA (ng/ml) |
| 1.5 | 1.5 | 105 |
| 3 | 2.5 | 111 |
| 6 | 3.4 | 130 |
| 9 | 8.2 | 107 |
| 24 | 1.5 | 68 |
| 36 | 0.3 | 24 |
| 48 | 0.02 | 6 |
| 72 | ND* | ND* |

*ND = not detectable

The urine concentration of copper$_2$indomethacin$_4$ was highest 9 hours after administration. After 48 hours the concentration was only 0.024 μg/ml and could not be detected in the urine after 72 hours.

Analytical methods were developed using GLC to allow quantification of copper$_2$indomethacin$_4$ in equine plasma and urine.

EXAMPLE 8

CLINICAL TRIALS

Clinical trials on racehorses were conducted using copper$_2$indomethacin$_4$ prepared as described in Example 1 in a paste. The trial was conducted over a period of 5 months. During this period 1000 doses each of phenylbutazone, indomethacin and copper$_2$indomethacin$_4$ were administered orally. The conclusions from the trial are:

1. A 200 mg dose of copper$_2$indomethacin$_4$ has comparable clinical anti-inflammatory effect to a 1 gm dose of phenylbutazone.
2. 200 gm of copper$_2$indomethacin$_4$ has a superior and more reliable effect compared to 200 mg of indomethacin.
3. There have been no observed side effects in the horses receiving copper$_2$indomethacin$_4$.

EXAMPLE 9

INDICATIONS TRIAL

Eighteen racehorses in training having clinical indications expected to respond to phenylbutazone were given copper$_2$indomethacin$_4$ prepared as described in Example 1, instead. The responses were graded "poor" if there was no response, "fair" if the clinical response was comparable or inferior to that expected from phenylbutazone, and "good" if the response was superior to the expectation had phenylbutazone been used. Fourteen responses were graded "good" and four were graded "fair". The clinical indications where the drug was rated "good" included bruised tendon, arthritis, pedal osteitis, navicular disease, myositis, shin-soreness and osteochondritis.

A summary of the results is as follows:

| Horse No. | Period of Administration | Dosage | Indication | Response |
| --- | --- | --- | --- | --- |
| 1 | 4 days | A | Bruised tendon (SDF) | Good |
| 2 | weeks | B | Pedal osteitis | Good |
| | Lameness recurred when treatment stopped | | | |
| 3 | weeks | B | Navicular disease | Good |
| 4 | 4 days | A | Jarred fetlocks | Good |
| 5 | weeks | B | Carpal arthritis | Good |
| 6 | weeks | B | Pedal osteitis | Good |
| 7 | weeks | B | Saccro-iliac subluxation | Fair |
| 8 | 4 days | B | Muscle soreness | Good |
| 9 | 4 days | B | Carpal arthritis | Good |
| 10 | weeks | B | Fetlock arthritis | Good |
| 11 | weeks | B | Shin soreness | Good |
| 12 | 4 days | A | OCD - shoulder | Good |
| 13 | 4 days | A | Acute sesamoiditis | Fair |
| 14 | weeks | B | Shin soreness | Fair–Good |
| 15 | 4 days | B | Muscle injury | Good |
| 16 | weeks | B | Post laminitis foot soreness & fetlock injury | Good |
| 17 | weeks | B | Navicular Disease | Good |
| 18 | 4 days | B | Carpal Injury - Cartilage only | Fair |

DOSAGE
A = 200 mg copper$_2$indomethacin$_4$/6 g paste twice daily;
B = 200 mg/6 g paste daily.

EXAMPLE 10

COMPARATIVE TOXICITY TRIAL IN HORSES

Melaena Index (measurement of occult blood in the faeces) was used to compare gastro-intestinal toxicity of copper$_2$indomethacin$_4$ (prepared as described in Example 1) with phenylbutazone in an identical paste base. Dosage range for both drugs was from normal therapeutic dose to 5X therapeutic dose. A control group received no medication. A positive index indicates gastro-intestinal toxicity. A zero index indicates lack of gastro-intestinal toxicity. A negative index indicates an improved melaena index during the trial.

| Group | Results Melaena Index |
| --- | --- |
| Controls | 0 |
| Copper$_2$indomethacin$_4$ | −100 |
| Phenylbutazone | +65 |

EXAMPLE 11

COMPARATIVE TOXICITY TRIAL IN DOGS

Ulcerogenic Index (measurement of area in cm$^2$ of gastro-intestinal ulceration of autopsy) was used to compare gastro-intestinal toxicity of identical doses of copper$_2$indomethacin$_4$ (prepared as described in Example 1) and indomethacin in an identical paste vehicle. Dosage range for both drugs was from 3X to 5X the therapeutic dose of indomethacin recommended for humans on a mg/Kg basis, and 7X to 11X the inventors' therapeutic dose of copper$_2$indomethacin$_4$.

| Drug | Mean No. of Ulcers | Ulcerogenic Index |
|---|---|---|
| Copper$_2$indomethacin$_4$ | 4 | 1.12 |
| Indomethacin | 4.75 | 2.16 |

EXAMPLE 12

CLINICAL TRIALS IN HUMANS

Copper2indomethacin$_4$ (prepared as described in Example 1) was administered orally to a group of adult men suffering from various types of arthritis and bursitis. There was clinical remission of symptoms and improved mobility, and none reported any symptoms of gut disturbance. One, a 53-year old bricklayer who had arthritis and bursitis in the right elbow unresponsive to other medication, was able to return to his trade.

INDUSTRIAL APPLICABILITY

It should be clear that the product, process and method of treatment will find wide use in the veterinary and medical fields.

The foregoing describes only some embodiments of the present invention and modifications obvious to those skilled in the art can be made thereto without departing from the scope of the invention.

We claim:

1. A method for the treatment of inflammation or pain in a mammal requiring such treatment, comprising administering to said mammal either:

a) an effective amount of a complex of indomethacin and a divalent transition metal selected from the group consisting of copper, zinc, cobalt and nickel, the complex having the formula

[M]$_2$[indomethacin]$_4$[X]$_n$, wherein

M is the divalent transition metal;

X is a tertiary amide of the following formula:

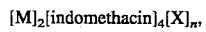

or an N-substituted lactam of the following formula:

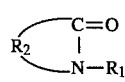

wherein R$_1$ is an alkyl having from 1 to 4 carbon atoms, and each R$_1$ may be the same or different, and R$_2$ is an alkylene having from 2 to 7 carbon atoms;

n is 2 or 3; or b) an effective amount of a pharmaceutical composition comprising said complex together with a pharmaceutically acceptable carrier, diluent, excipient, or combinations thereof.

2. The method as defined in claim 1 wherein the complex or the pharmaceutical composition is administered orally, parenterally, rectally or topically.

3. The method as defined in claim 1 wherein the divalent transition metal is copper.

4. The method as defined in any one of claims 1, 2 or 3 wherein the amount of the complex used is from about 0.03 to about 0.5 mg of said complex per kg of said mammal.

5. The method as defined in claim 4 wherein the amount of complex used is from about 0.1 to about 0.2 mg of said complex per kg of said mammal.

6. The method of claim 1 wherein the mammal is a human, horse or dog.

7. A pharmaceutical composition comprising:

a pharmaceutically acceptable carrier, diluent, excipient or combinations thereof; and a complex of indomethacin and a divalent transition metal selected from the group consisting of copper, zinc, cobalt and nickel, the complex having the formula

[M]$_2$[indomethacin]$_4$[X]$_n$, wherein

M is the divalent transition metal;

X is a tertiary amide of the following formula:

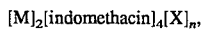

or an N-substituted lactam of the following formula:

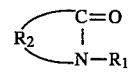

wherein R$_1$ is an alkyl having from 1 to 4 carbon atoms, and each R$_1$ may be the same or different, and R$_2$ is an alkylene having from 2 to 7 carbon atoms; and n is 2 or 3.

8. The composition as defined in claim 7 wherein M is copper.

9. The composition of claim 7 wherein X is selected from the group consisting of dimethylformamide, N-methylpyrrolidone, dimethyl acetamide and mixtures thereof.

10. The composition of claim 9 wherein the complex is copper$_2$[indomethacin]$_4$[dimethylformamide]$_n$, wherein n is 2 or 3.

11. A complex of indomethacin and a divalent transition metal selected from the group consisting of copper, zinc, cobalt and nickel, the complex having the formula

[M]$_2$[indomethacin]$_4$[X]$_n$, wherein

M is the divalent transition metal;

X is a tertiary amide of the following formula:

or an N-substituted lactam of the following formula:

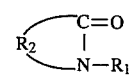

wherein R$_1$ is an alkyl having from 1 to 4 carbon atoms, and each R$_1$ may be the same or different, and R$_2$ is an alkylene having from 2 to 7 carbon atoms; and n is 2 or 3.

12. The complex of claim 11 wherein M is copper.

13. The complex of claim 11 wherein X is selected from the group consisting of dimethylformamide, N-methylpyrrolidone, dimethyl acetamide and mixtures thereof.

14. The complex of claim 13 which is copper$_2$[indomethacin]$_4$[dimethylformamide]$_n$, wherein n is 2 or 3.

* * * * *

UNITED STATES PATENT AND TRADEMARK OFFICE
CERTIFICATE OF CORRECTION

PATENT NO.   : 5,466,824
DATED        : November 14, 1995
INVENTOR(S)  : Hubertus L. Regtop et al.

It is certified that error appears in the above-indentified patent and that said Letters Patent is hereby corrected as shown below:

<u>On the Title Page</u>

Under the heading "Foreign Application Priority Data", column 1, line 2, please insert the following information: --PCT/AU90/00209 dated 5/21/90--.

Under the heading "OTHER PUBLICATIONS", column 1, line 1, please delete "Quellette" and substitute --Ouellette--.

Signed and Sealed this

Twenty-fourth Day of September, 1996

Attest:

BRUCE LEHMAN

*Attesting Officer*     *Commissioner of Patents and Trademarks*